(12) United States Patent
Wollnik

(10) Patent No.: US 8,067,747 B2
(45) Date of Patent: Nov. 29, 2011

(54) PARALLEL PLATE ELECTRODE ARRANGEMENT APPARATUS AND METHOD

(75) Inventor: Hermann Wollnik, Santa Fe, NM (US)

(73) Assignee: Shimadzu Corporation, Kyoto-fu (JP)

( * ) Notice: Subject to any disclaimer, the term of this patent is extended or adjusted under 35 U.S.C. 154(b) by 312 days.

(21) Appl. No.: 12/301,728

(22) PCT Filed: May 22, 2006

(86) PCT No.: PCT/US2006/019747
§ 371 (c)(1),
(2), (4) Date: Nov. 20, 2008

(87) PCT Pub. No.: WO2007/136373
PCT Pub. Date: Nov. 29, 2007

(65) Prior Publication Data
US 2009/0206250 A1    Aug. 20, 2009

(51) Int. Cl.
*H01J 3/14* (2006.01)
(52) U.S. Cl. .................... 250/396 R; 250/281; 250/282; 250/290; 250/292
(58) Field of Classification Search .............. 250/396 R, 250/281, 282, 290, 292
See application file for complete search history.

(56) References Cited

U.S. PATENT DOCUMENTS
7,012,250 B1 * 3/2006 Aksyuk et al. ................ 250/292

OTHER PUBLICATIONS

H. Wollnik, "Optics of Charged Particles", 1987, pp. 48-89, Academic. Press, Orlando.
G. Eiceman, et al., $2^{nd}$ Ed. "Ion Mobility Spectrometry" Part II, 2006, pp. 116-240, Taylor & Francis, CRC-Press, Boca Raton.
P.H. Dawson, "Quadrupole Mass Spectrometry and its Application", Chapter II, 1976, pp. 9-63, Elsevier, Amsterdam.

* cited by examiner

*Primary Examiner* — Michael Maskell
(74) *Attorney, Agent, or Firm* — Sughrue Mion, PLLC

(57) ABSTRACT

A system for guiding an ion beam along an axis (Z), comprises at least one section having upper flat plate strip electrodes (1u, 2u, 3u, 4u and 5u) and lower flat plate strip electrodes (1d, 2d, 3d, 4d and 5d) for producing at least one electric field of substantially symmetric in a parallel direction and substantially antisymmetric in a perpendicular direction with respect to a plane including a beam axis and a fringe-field boundary that is located at the end of the at least one section.

50 Claims, 17 Drawing Sheets

PARALLEL PLATE ELECTRODE ARRANGEMENT APPARATUS AND METHOD

BACKGROUND OF THE RELATED ART

1. Technical Field

The present invention relates to a charged-particle transport device in which a system of electrodes is installed in that is designed to transversally focus the charged particles. More specifically, the present invention relates to forming the required transverse fields by electrode strips on flat plates arranged in a substantially parallel configuration, and variations and applications thereof.

2. Related Art

In the related art, charged particles are transported in vacuum or in a buffer gas with transverse forces caused by electric multipole fields formed by rod-like electrodes that are arranged parallel to and around the particle beam. Such fields can be DC-field, i.e. constant direct current fields, or RF-fields, i.e. quickly varying high-frequency fields. Such fields are important for many applications in which the transport of charged particles is required over reasonably long distances without intensity losses. Generally these applications can be characterized by the pressure of the buffer gas in the transport region or the residual gas pressure in a vacuum.

Related art particle transport schemes include:

1. The transport of charged particles in a region in which the buffer gas has pressures from several mbar to several bar. As discussed in [G. Eiceman, "Ion Mobility Spectrometry", CRC-Press, Boca Raton, 2006] one can house in such a region:
   1.1. an ion-mobility spectrometer (IMS) or
   1.2. a differential mobility spectrometer (DMS) also known as FAIMS.
2. The transport of charged particles in a region in which the buffer gas has pressures from below µbar to several mbar. In such a region one can house:
   2.1 a "beam-cooler" in which ions collide with atoms or molecules of the buffer gas and in this process distribute kinetic energy to them. Thus the ions will be "cooled" and the phase-space the ion beam occupies be reduced.
   2.2 a "collision cell" in which molecular ions will be broken into fragments by collisions with atoms or molecules of the buffer gas.
   2.3 a "transfer line" in which ions can be transported from a high pressure region to a low pressure region or vice versa.
3. The transport of charged particles in a region in which the residual gas pressure is lower than about one µbar. In such a region one can house
   3.1 a beam transport channel as in particle accelerators or particle-beam guidance systems or
   3.2 a mass spectrometer built from a sector field, an RF-quadrupole or an energy-isochronous time-of-flight system [P. H. Dawson, "Quadrupole Mass Spectrometry and its Application", Elsevier, Amsterdam 1976]

In the foregoing examples, it is important that substantially all (or at least a large portion of) the initially existing charged particles arrive at the end of the transport line. In the related art, this can be achieved by using one or a number of lenses that repeatedly refocus the charged particle beam along the transport line with a curvilinear beam axis Z.

Assuming Cartesian X,Y coordinates perpendicular to this beam axis, rotationally symmetric electric or magnetic lenses can be used to simultaneously focus the charged particles towards the beam axis in X- and in Y-direction. However, magnetic or electric quadrupole lenses, i.e. 4-poles, can also be used advantageously to focus the charged particles in either the X- or the Y-direction and defocus them in the other direction, as discussed in [H. Wollnik, "Optics of Charged Particles", Acad. Press, Orlando, 1987].

In some cases, magnetic or electric hexapoles or octupoles, i.e. 6-poles or 8-poles, can be used that exhibit nonlinear forces that drive the charged particles towards or away from the beam axis. In all 4-, 6-, or 8-pole devices—usually referred to as multipoles—the overall action on the charged particles is such that the charged particles are driven towards the beam axis both in X- and in Y-directions. This overall action occurs because the charged particles experience overall larger forces towards rather than away from the beam axis in each multipole. The reason is that these forces increase with the distance from the axis when they pass through a multipole, and since the beam diameters are always larger when the particles experience forces towards the beam axis, while the beam diameters are smaller when the particles experience forces away from the beam axis.

Although beams of charged particles can be transported efficiently by separated short 4-, 6-, and 8-pole devices, it is also possible to use a longer single device if one applies high-frequency RF-potentials to its electrodes [P. H. Dawson, "Quadrupole Mass Spectrometry and its Application", Elsevier, Amsterdam 1976]. In this case, an ion will experience similar focusing and defocusing forces during its passage through the RF-multipole.

In the related art, electric multipoles are formed by $2N=4, 6, 8 \ldots$ rod-like electrodes arranged parallel to and around the ion beam axis at equal azimuthal intervals $\Delta\theta=\pi/N$ in which case one applies to the even-numbered electrodes, the potential $+V_{N0}$, and to the odd-numbered electrodes the potential $-V_{N0}$. The most common multipoles are quadrupoles that have $2N=4$ poles the geometry, as illustrated in FIG. 1, characterized by 4 electrodes arranged at azimuthal intervals of $\pi/2$ around an aperture of diameter $2G_0$.

In cylindrical $R,\theta,Z$-coordinates, the potential $V_N(R,\theta)$ in a 2N-pole is independent of Z, and can be described as:

$$V_N(R,\theta) = V_{N0}(R/G_0)^N * \cos[N(\theta-\Phi)] \qquad (1)$$

Here, $\theta$ is the azimuthal angle around the Z-axis, and $\Phi$ is the azimuthal angle by which the arrangement of the 2N electrodes has been rotated relative to the $\theta=0$ plane, i.e. the XZ-plane in FIG. 1. However, the exact potential distribution of Eq. (1) is usually only approximated when realistic electrodes are used that have finite shape tolerances.

In case of a classical electric 2N-pole with $N=2$, as is shown in FIG. 1, the potential distribution $V_2(R, \theta-\Phi)$ of Eq. (1) is approximated by applying potentials $+V_{20}, -V_{20}, +V_{20}, -V_{20}$ to electrodes with apices at $\theta-\Phi=0, \pi/2, \pi, 3\pi/4$, and with $\theta$ being the azimuthal angle. In order to represent $V_2(R, \theta-\Phi)$ of Eq. (1) exactly, the electrodes must be hyperbolically shaped in the XY-plane. Due to the symmetry of the electrodes, the potential distribution $V(R, \theta-\Phi)$ has a 4-fold symmetry with $\Phi$ being the angle by which the electrode arrangement has been rotated relative to $\theta=0$ as is illustrated in FIG. 1 for the cases $\Phi=0$ and $\Phi=\pi/4$. The potential vanishes along the dashed lines in FIG. 1 while the field $E_2=\text{grad}V_2(G_0)$ is constant along the so-called aperture circle of diameter $2G_0$. The resulting forces on charged particles thus have a constant magnitude along this circle but change direction as indicated by the small arrows in FIG. 1.

SUMMARY OF THE INVENTION

Aspects of the exemplary embodiments are directed to a system for guiding an ion beam along a substantially continuous beam axis through at least one field that exerts a force on ions in the beam, the system comprising at least one section comprising a substantially flat plate-multipole having an upper flat plate and a lower flat plate, wherein the force is one of substantially symmetric in a parallel direction and substantially antisymmetric in a perpendicular direction with respect to a plane that includes the beam axis, each of the upper flat plate and the lower flat plate comprising a plurality of first electrode strips having corresponding potentials, the first electrode strips generating at least a portion of the at least one field, wherein a fringe-field boundary is located at each end of the at least one section, and the first electrode strips are substantially thin and flat.

In the system, the upper flat plate and the lower flat plate are positioned one of substantially parallel and inclined to the plane in the at least one section where an extrapolated intersection line of the upper flat plate and the lower flat plate is substantially perpendicular to the ion beam axis.

In the system, the at least one section comprises at least one of a straight section and a curved section that is curved within the plane, and wherein the straight ones of the at least one section include substantially quadrilateral ones of the first electrode strips parallel to the ion-beam axis, and curved ones of the at least one section include substantially curved ones of the first electrode strips having a substantially constant distance from the ion-beam axis.

In the system, the ion-beam axis at the at least one section is at least one of straight, curved, and curvilinear.

In the system, each of the first electrode strips have at least one of (a) a straight edge and (b) a curved edge, and the width substantially perpendicular to the ion-beam axis is less than the length along the ion-beam axis for each of the first electrode strips. Further, one of the lengths and the angles of deflection of the first electrode strips are equal with respect to at least one adjacent one of the first electrode strips. Also, one of the lengths and the angles of deflection of the first electrode strips are not equal with respect to at least one adjacent one of the first electrode strips, and vary one of linearly and non-linearly with their respective distances from the ion-beam axis.

In the system, the width of at least one of the first electrode strips increases along the ion-beam axis. Further, a ratio of the widths of the first electrode strips with respect to a distance between the upper flat plate and the lower flat plate is one of constant and variable along the ion-beam axis. Also, potentials are applied to at least two of the first electrode strips for a period, so as to form a field along the ion-beam axis.

In the system, the width of at least one of the first electrode strips increases and decreases along the ion-beam axis, such that the width is maximized at a middle portion.

In the system, widths of ones of the first electrode strips are greater at further distances from the ion beam.

In the system, the width of a central one of the first electrode strips is equal or greater than the widths of adjacent ones of the first electrode strips.

In the system, the ions are directed toward one of the upper flat plate and the lower flat plate having a greater ion-attracting potential applied thereto for a period, and an aperture therein so as to permit emission of at least a portion of the ions.

In the system, the ions are directed along the plane by different potentials applied to the first electrode strips to form a field parallel to the plane, for a period.

The system further comprises a plurality of second electrode strips positioned substantially perpendicular to the plane at a first surface and a second surface, wherein the second electrode strips are substantially thin and flat. In the system, the second electrode strips are one of (a) substantially quadrilateral and (b) substantially curved and having a constant minimal distance from the ion-beam axis. Also, widths of the second electrode strips are greater at distances further from the plane. Further, the width of at least one of the second electrode strips increases along the ion-beam axis. Additionally, the width of at least one of the second electrode strips increases and decreases along the ion-beam axis, such that the width is maximized at a middle portion. Further, the ions are directed toward one of the first surface and the second surface having a greater ion-attracting potential applied to the second electrode strips thereat for a period, and an aperture in the first surface and the second surface to permit emission of at least a portion of the ions. Also in the system, the plate-multipole is used for ion beam transport in a low-pressure buffer-gas, in a vacuum ion-transport system in which the residual gas pressure is so low that an ion experiences substantially minimal ion-atom or ion-molecule collisions, RF multipole fields and DC multipole fields are formed as to provide mass analyzing capabilities, and a distance between the first surface and the second surface is substantially less than a distance between the upper flat plate and the lower flat plate. Additionally in the system, at least one of (a) substantially constant potentials and (b) sinusoidal potentials are applied to each of the second electrode strips. Further in the system, at least one of (a) substantially constant potentials and (b) rectangularly switched potentials are applied to each of the second electrode strips. Also, at least one of the RF potentials comprises at least one frequency applied to one of the second electrode strips, and each the at least one frequency can vary with respect to each other in at least one of amplitude and phase.

In the system, the first electrode strips comprise one of conductive material and material that has a conductive surface, such that the potential along each of the electrode strips is substantially constant.

In the system, the first electrode strips are formed as groups of one or more wires.

In the system, the first electrode strips comprise patches of conductive material on respective insulating or slightly conducting substrates, and are formed as printed circuit boards. Also, the patches are separated by an area that is less than or equal to a thickness of any one of the first electrode strips. Further, a conductive layer is provided that is configured to shield a high-frequency field formed by the patches if RF potentials are applied.

In the system, at least one of the RF potentials comprises at least one frequency applied to one of the first electrode strips, and each the at least one frequency can vary with respect to each other in at least one of amplitude and phase. Also, at least the dipole field is modulated by a frequency independent of other multipole fields for the at least one section.

In the system, at least one of (a) substantially constant potentials and (b) sinusoidal potentials are applied to each of the first electrode strips.

In the system, at least one of (a) substantially constant potentials and (b) rectangularly switched potentials are applied to each of the first electrode strips.

In the system, outer ones of the first electrode strips are at a common potential, and non-central inner ones of the first electrode strips have a substantially greater potential than the common potential, and a central one of the first electrode strips has a substantially lesser potential than that of the inner ones of the first electrode strips.

In the system, the plate-multipole is used for ion beam focusing toward the plane in a high-pressure buffer-gas from several bar to below 1 mbar in an ion mobility spectrometer (IMS) or in a differential mobility spectrometer (DMS), wherein RF multipole fields and DC multipole fields are provided by the plate-multipole as the ions travel along the ion-beam axis.

In the system, the plate-multipole is used for ion beam transport in a medium-pressure buffer-gas from about 1 mbar to below 1 μbar in a beam cooler in which the ions lose energy in ion-atom or ion-molecule collisions so that the phase-space of the ion beam is reduced wherein RF multipole fields are provided at the plate-multipole as the ions travel along the ion beam axis.

In the system, the plate-multipole is used for ion beam transport in a medium-pressure buffer-gas from about 1 mbar to below 1 μbar in a collision chamber in which molecules are fragmented in ion-atom or ion-molecule collisions and fragment ions are extracted.

In the system, the plate-multipole is used for ion beam transport in a low-pressure buffer-gas, in a vacuum ion-transport system in which the residual gas pressure is so low that an ion experiences substantially minimal ion-atom or ion-molecule collisions, and RF multipole fields and DC multipole fields are formed as to provide mass analyzing capabilities.

In the system, the field of the plate-multipoles is limited by substantially rectangular, rotational, slit-type electrodes or grids placed at potentials that are ion repelling relative to the ion-beam axis, so that ions inside the plate-multipole are trapped as in a linear quadrupole ion trap, and wherein RF multipole fields and DC multipole fields are formed as to provide mass analyzing capabilities.

BRIEF DESCRIPTION OF THE DRAWINGS

The above aspects and features of the exemplary embodiments will be more apparent by describing certain embodiments of the present invention with reference to the accompanying drawings.

FIG. 7 illustrates an exemplary embodiment of two possible ways to provide a DC-field in Z-direction in the arrangement of electrode strips of FIG. 2 or of FIG. 5 by the use of "tapered first electrode strips" as in FIG. 6. In the shown examples the electrode strips are arranged on two parallel plates where in example A the same RF- and DC-potential that is supplied to the electrode strips 3 is also supplied to the electrode strips 3a though to these electrode strips some DC- and RF-potential can be added. In example B the same is done for the electrode strips 2a, 3a, and 4a.

FIG. 15 also illustrates how the different potentials can be fed to the different electrodes by leads to the plates at Lu and Ld located between grounded plates G2u, G1u and G1d,G2d, respectively, as can be done in the technique of multilayered printed circuit boards.

In FIG. 16, however, the active elements are placed very close to the electrode strips so that the necessary RF-power is reduced, as are the generated RF-stray fields. These active elements are shown to be housed in an enclosure in which the residual gas pressure may differ from that in which the ions move. In some cases, watercooling Cu and Cd may be provided to this enclosure.

DETAILED DESCRIPTION OF THE EXEMPLARY EMBODIMENTS

Figure 1:
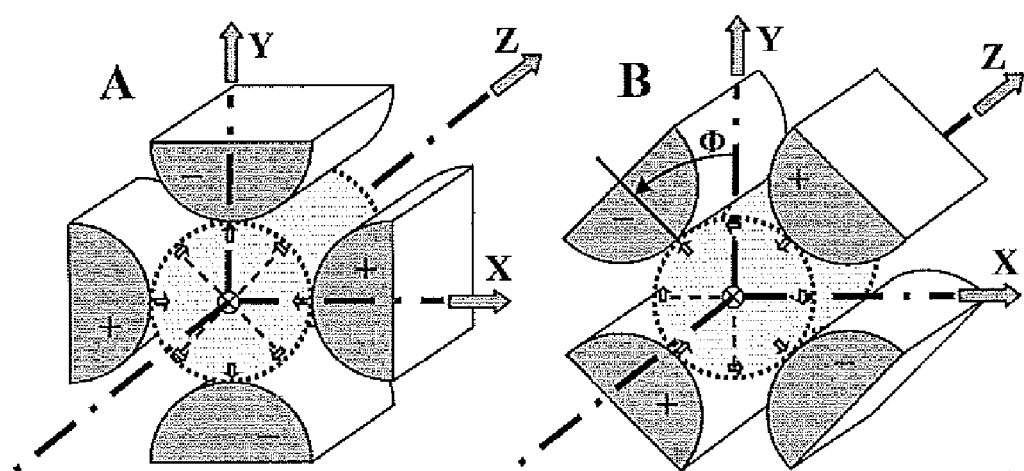
FIG. 1 illustrates the electrode geometry of a related art electric 4-pole with rod-type electrodes that have apices at $\theta - \Phi = 0, \pi/2, \pi, 3\pi/4$ and with $\theta$ being the azimuthal angle. In example A such an electrode arrangement is shown for $\Phi = 0$ and in example B for $\Phi = \pi/4$.

Exemplary embodiments of the present invention will be described in greater detail with reference to the accompanying drawings. In the following description, the same drawing reference numerals are used for the same elements even in different drawings. The matters defined in the description such as a detailed construction and a shape of elements are nothing but the ones provided to assist in a comprehensive understanding of the invention. Thus, it is apparent that the present invention can be carried out without those defined matters. Also, well-known functions or constructions are not described in detail since they would obscure the invention in unnecessary detail.

Figure 2:
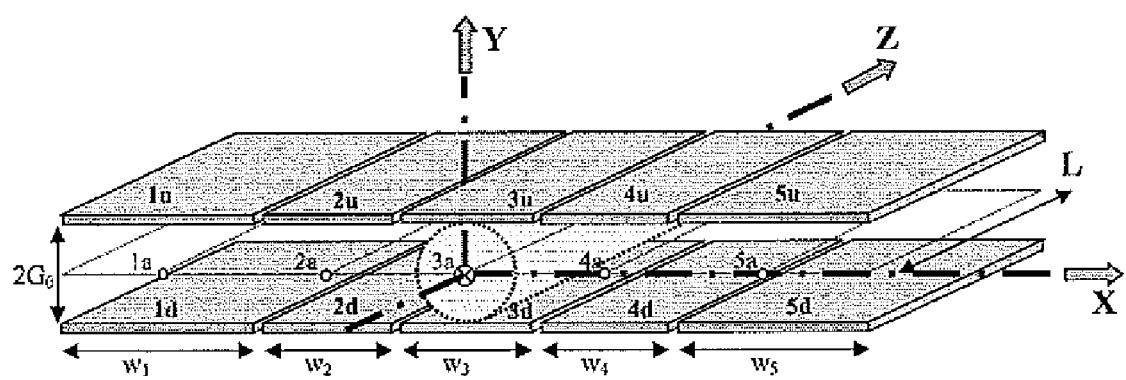
FIG. 2 illustrates an exemplary embodiment of flat and thin first electrode strips of length L arranged on two parallel plates separated by a distance $2G_0$. Characterizing the different electrode strips by the positions of the centers X,Y of their widths $w_1, w_2, w_3, w_4, w_5$ and applying to these electrode strips potentials that are substantially identical to those found at positions X,Y in a related art multipole with rod-type electrodes, one will obtain a similar multipole potential distribution.

FIG. 2 illustrates an exemplary embodiment of the present invention to produce the superposition of multipole potential distributions by twice 5 electrode strips though smaller or larger numbers of electrode strips are recommendable in many cases. An arrangement of electrode strips is provided on parallel plates separated by a distance $2G_0$ so that the same aperture diameter is available as in a related art quadrupole shown in FIG. 1. In the shown FIG. 2 there are 5 electrode strips on each plate of widths $w_1,w_2,w_3,w_4,w_5$, where $w_1$ and $w_5$ are larger than the other electrode strips and principally can extend to very large values of X and -X. Further, points $1a,2a,3a,4a,5a$ are marked in the midplane, as well as lines that pass through these points and are parallel to the Z-axis. However, as a simplification of the arrangement of electrode strips in FIG. 2:

the positions and widths of the electrode strips are shown to be substantially symmetric to X and that the widths of the different electrode strips are shown to be substantially identical in the upper and the lower plates, i.e. that they are also substantially symmetric to Y.

However, plate-multipoles (i.e., an upper plate and a lower plate substantially parallel to each other, each having thin and flat electrode strips) could also be constructed if the electrode strips would be asymmetrical to X or to Y or asymmetrical to both.

Though the potential distribution of a 2N-pole as described by Eq. (1) can be obtained for $N \geq 2$ by rod-type electrodes arranged at different azimuthal positions separated by $\Delta\theta = \pi/N$ around a beam axis at equal distances $G_0$, the substantially same distribution can be produced or at least approximated by thin flat electrode strips on parallel plates (also referred to as "plate-multipoles") separated by a distance $2G_0$. The electrode strips on these planar surfaces can be formed with high mechanical precision, such that the potential distribution can be reproduced exactly from one instrument to the next. Also this arrangement of electrode strips allows one to build a system for which $2G_0$ is substantially small and also a multipole for N=1, i.e. a dipole, which can be formed with high precision.

Establishing an XZ-plane in the middle between the shown plates in FIG. 2 the plates are situated at $Y_0 = \pm G_0$, the positions of electrode strips and thus the points at which Eq. (1) must be evaluated are found from $\theta = \arctan(G_0/X)$ and $R = G_0/\sin\theta$ where X is approximately the position of the center of each strip. In this arrangement of electrode strips, the mentioned precise dipole potential distribution (N=1) is added to the established multipole potential distribution by increasing the potentials of all electrode strips at $Y = \pm G_0$ by $\pm V_{10}$.

For such two-plate arrangements of electrode strips, it is advantageous to describe the potential distribution $V_N$ not in cylindrical Coordinates but rather in a Cartesian X-Y-Z-coordinate system. In this case Eq. (1) must be rewritten as:

$$V_N(X,Y) = (V_{N0}/G_0^N)[\cos(N\Phi)*RE(X+iY)^N + i*\sin(N\Phi)*IM(X+iY)^N] \quad (2)$$

In the region between the plates of FIG. 2, i.e. for $-G_0 \leq Y \leq G_0$, for N=1, 2, 3, 4 . . . one finds:

$$N=1: V_1(X,Y) = (V_{10}/G_0)[X*\cos(\Phi) - Y*\sin(\Phi)] \quad (3a)$$

$$N=2: V_2(X,Y) = (V_{20}/G_0^2)[(X^2-Y^2)*\cos(2\Phi) - (\pm 2XY)*\sin(2\Phi)] \quad (3b)$$

$$N=3: V_3(X,Y) = (V_{30}/G_0^3)[(X^2-3Y^2)X*\cos(3\Phi) - (3X^2-Y^2)Y*\sin(3\Phi)] \quad (3c)$$

$$N=4: V_4(X,Y) = (V_{40}/G_0^4)[(X^4-6X^2Y^2+Y^4)*\cos(4\Phi) - (X^2-Y^2)(\pm 4XY)*\sin(4\Phi)] \quad (3d)$$

with $V_{N0}$ being the maximum potential at a point of the aperture circle of diameter $2G_0$. If one wants to form potential distributions characterized by $\Phi=0$, the potentials on electrode strips at $+X$ and $-X$ must be substantially equal, provided that the electrodes themselves are arranged symmetrically to $X=0$.

In case of a substantially high number of electrode strips arranged at different X-values on two such parallel plates characterized by $Y=\pm G_0$, one can use Eqs. (3)(a)-(d) as shown above to determine the proper potentials $V(X,\pm G_0)$ of the electrode strips:

$$N=1: V_1(X,\pm G_0)=V_{10}\{(X/G_0)*\cos(\Phi)-[\pm\sin(\Phi)]\} \quad (4a)$$

$$N=2: V_2(X,\pm G_0)=V_{20}\{[(X/G_0)^2-1]\cos(2\Phi)-(\pm 2x/G_0)\sin(2\Phi)\} \quad (4b)$$

$$N=3: V_3(X,\pm G_0)=V_{30}\{(X/G_0)[(X/G_0)^2-3]\cos(3\Phi)\pm[1-3(X/G_0)^2]\sin(3\Phi)\} \quad (4c)$$

$$N=4: V_4(X,\pm G_0)=V_{40}\{[(X/G_0)^4-6(X/G_0)^2+1]\cos(4\Phi)\pm(4X/G_0)[1-(X/G_0)^2]\sin(4\Phi)\} \quad (4d)$$

When the electrode strips are not characterized by a single X-value but when they rather extend over a range of X, the potentials one would determine from Eqs. (4a)-(4d) are only approximate values and the finally obtained potential distribution only approximates a summation of $V_N(X,Y)$ the desired superposition of multipole potentials. However, the corresponding potential distribution can be determined accurately by numerically solving Laplace's equation with the geometry and the potentials of the electrode strips being the boundary conditions. Having thus obtained the potential distribution along a circle of diameter $2G_0$ shown in FIG. 2, one finds the magnitudes of the different multipole components from a Fourier analysis of this potential distribution. The reason is that the magnitudes of the different 2N-poles vary along this circle as $\cos[N(\theta-\Phi)]$. By changing the potentials of the different electrodes, one can approximate the desired superposition of multipoles. This result can then iteratively be refined by repeating this procedure for differently chosen X-widths of the different electrode strips.

Figure 3:
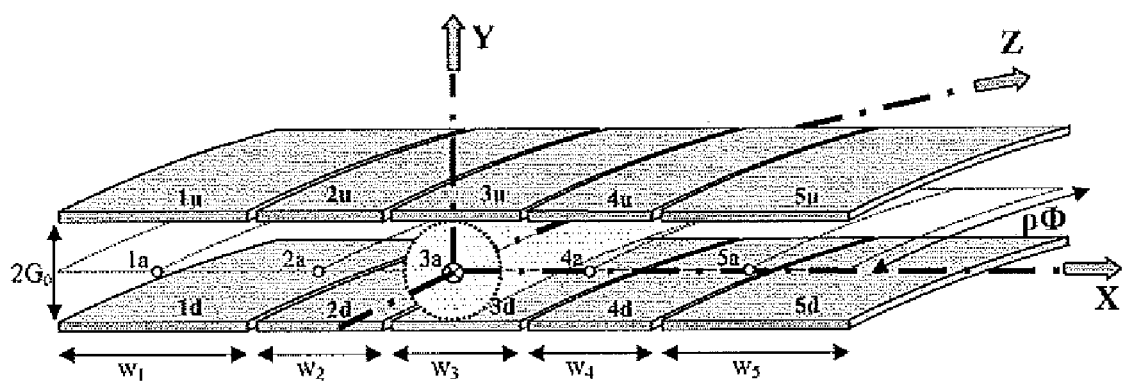
FIG. 3 illustrates an exemplary embodiment of flat and thin first electrode strips arranged on two parallel plates separated by a distance $2G_0$ as in FIG. 2. In the here shown example the electrode strips are curved and thus are ring segments if the beam axis Z is a circle of radius p that has an angle of deflection of $\Phi$. The average lengths of the different electrode strips are from left to right: $\Phi[\rho+(w_1/2+w_2+w_3/2)]$, $\Phi[\rho+(w_2+w_3)/2]$, $\Phi\rho$, $\Phi[\rho-(w_3+w_4)/2]$, $\Phi[\rho-(w_3/2-w_4-w_5/2)]$.

Though in many cases the Z-axis, i.e. the axis of the ion beam, is desired to be straight, there are cases in which this axis is desired to be curved or even circular. A corresponding field of a "toroidal condenser" as explained in [H. Wollnik, "Optics of Charged Particles", Acad Press, Orlando 1987] can be formed by an arrangement of electrode strips that is similar to FIG. 2 and is illustrated in FIG. 3 in which the quadrilateral (for example, but not by way of limitation, rectangular or trapezoid-shaped) electrode strips of FIG. 2 are replaced by curved (for example but not by way of limitation, ring-shaped) segments. Similarly to FIG. 2 also in FIG. 3 only twice 5 electrode strips are shown though smaller or larger numbers of electrode strips are recommendable in many cases. If the potentials of the different curved segments differ, a field in the radial direction, i.e. the X-direction in FIG. 3, can be established, in which case the beam axis is substantially circular and situated within the XZ-plane that also contains its center of curvature. This arrangement of electrode shown in FIG. 3 allows the substantially same aperture diameter $2G_0$ as in FIG. 2. Similarly as in FIG. 2 also in FIG. 3 there are 5 electrode strips shown on each plate having widths $w_1, w_2, w_3, w_4, w_5$, where $w_1$ and $w_5$ have been chosen to be larger than the other electrode strips. Additionally, points $1a, 2a, 3a, 4a, 5a$ are marked in the midplane, as well as lines that go through these points and that are concentric to the curved Z-axis. This concentricity is here referred to as parallelism.

Though in FIG. 2 and in FIG. 3 the electrode strips are all shown to substantially the same widths it can be of advantage to choose them noticeably different. In order to define the potentials close to the ion beam especially precise one can for instance cut one or several of the electrode strips close to the ion beam into several small electrode strips to which slightly different potentials can be applied. One can, however also choose the center electrode strip wider than the neighboring one, which—in case this center electrode strip is substantially wider than the plate separation—will increase the 8-pole component of the multipole potential distribution.

Figure 4:
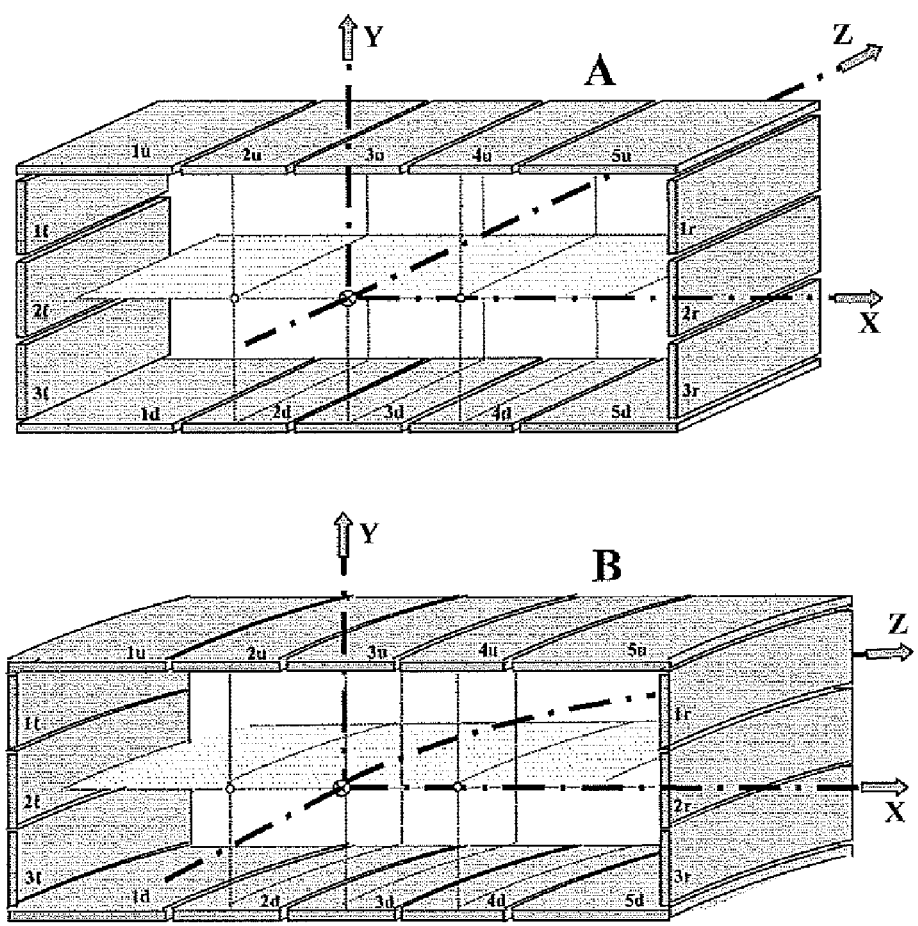
FIG. 4 illustrates an exemplary embodiment of flat and thin first electrode strips arranged on two plates at $Y_u$ and $Y_d$ plus flat and thin second electrode strips arranged on two orthogonally mounted surfaces placed at $X_l$ and $X_r$. This arrangement of electrode strips is shown A for a straight ion beam axis Z and B for a curved ion beam axis Z.

The arrangements of electrode strips shown in FIG. 2 can achieve precise quadrupole or other multi-pole fields with a straight axis and the arrangement of electrode strips shown in FIG. 3 that of a toroidal condenser which has a circular Z-axis. At least for larger values of $G_0$, however, a substantially wide structure is required in X-direction. This wide structure can be made smaller by adding to the electrode strips on the parallel plates at $Y_u$ and $Y_d$ further additional electrode strips on surfaces that cross the XZ-reference plane perpendicularly, i.e. on ortho-surfaces as referred to here. In the case of a straight Z-axis in such systems, the electrode strips on the plates at $Y_u$ and $Y_d$ and the electrode strips on the ortho-surfaces at $X_l$ and $X_r$ would substantially be rectangles. In the case of a curved Z-axis the electrode strips on the plates at $Y_u$ and $Y_d$ would substantially be ring segments and the electrode strips on the ortho-surfaces would substantially be cylinders. The shapes of these se electrode strips are illustrated in FIG. 4. In such a system, a rectangular multipole field region is formed for which the potential distribution along the ortho-surfaces at $X_l$ and $X_r$ limits the fields to the largest and smallest X-values while the precision of the potential distribution is substantially determined by the shape and the potentials of the electrode strips on the parallel plates at $Y_u$ and $Y_d$.

Though it is often recommendable to use, in addition to electrode strips at the parallel plates, also additional electrode strips on ortho-surfaces, it should be noted that the same desired potential distributions can be obtained by electrode strips on the parallel plates only without the aid of electrode strips on ortho-surfaces. In such cases, the potential distribution within the aperture circle of diameter $2G_0$ is predominantly shaped by the widths w of the electrode strips 2, 3, 4 and of their potentials. There are similar though much smaller influences by the electrode strips 1 and 5. It is important to note that such changes will also influence the potential on points along the Z-axis. However, to keep the potential of the Z-axis unchanged one can always add or subtract a certain potential RF- and DC-potential $V_u$ to all electrode strips in the upper plate and another RF- and DC-potential $V_d$ to all electrode strips in the lower plate.

In case the potentials of the electrode strips 1 and 5 are chosen to be at ground potential and that the electrode strips 3 are approximately at this potential also, it is usually possible to find suitable field arrangements by applying potentials to the electrode strips 2 and 4 which both are substantially identical to a value $V_0$. In case the electrode strips 2, 3, 4 are all approximately $2G_0$ wide, i.e. $w_2=w_3=w_4=2G_0$, one finds for instance that the potential distribution around the Z-axis is substantially that of a pure quadrupole as described in Eq. (1) for N=2 for which $V_{20}$ is a sizeable fraction of $V_0$.

Calculating numerically the potentials $V_1, V_2, V_3, V_4, V_5$ of the points $1a, 2a, 3a, 4a, 5a$ in FIG. 2 and in FIG. 3 that characterize the middles of the gaps between each u,d-pair of electrode strips of different widths $w_2$ and $w_4$ that the potentials $V_2$ and $V_4$ substantially increase with the ratios of $w_2/G_0$ and $w_4/G_0$ and that the small potentials $V_1, V_3, V_5$ show similar dependencies.

Though the detailed potential distribution between the electrode strips on the two parallel plates should be determined numerically, it is possible to state that, for with Z varying separations 2G(Z) and widths w(Z) of the different electrode strips the potential along the Z-axis remains approximately constant if the (w/G)-ratio does not vary substantially with Z. In such cases, one thus can expect that the multipole strengths increase or decrease with Z. In other cases, more complex field distributions must be expected, as well as the appearance of a field in Z-direction. In those cases on thus finds that applying RF-potentials to the different electrode strips there will be RF-forces on the ions in Z-direction and applying DC-potentials to the different electrode strips, the ions will be accelerated or decelerated in Z-direction.

Figure 5:
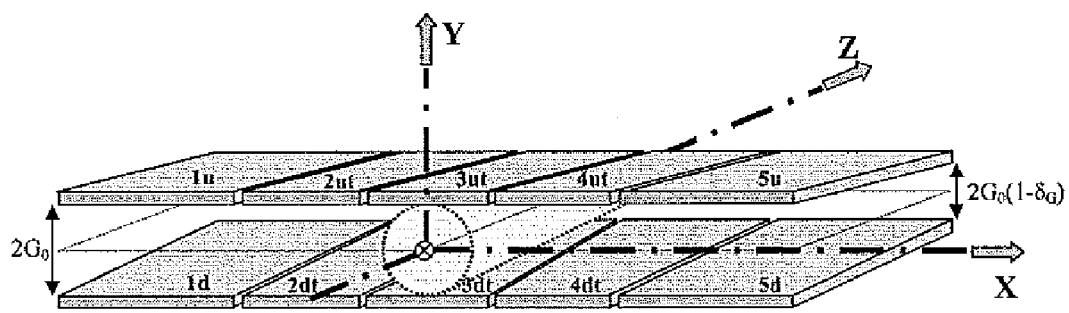
FIG. 5 illustrates an exemplary embodiment of the arrangement of electrode strips which is a variation of FIG. 2 showing flat and thin first electrode strips arranged on two plates that are inclined relative to each other so that their separation 2G(Z) varies with Z. This causes a varying multipole strength along the Z-coordinate and also fields in Z-direction.

A change of the said w/G-ratio can be achieved
1. by reducing G(Z) with increasing Z from $G_0$ to $G_0(1-\delta_G)$ over the lengths of the electrode strips, for example by inclining the two plates relative to each other, as is indicated in FIG. 5, and
2. by using "tapered quadrilateral" electrode strips (see FIG. 6) as compared to the "rectangular" electrode strips of FIG. 2 or by using "tapered curved" electrode strips (not shown in a figure) as compared to the "curved" electrode strips of FIG. 3, i.e. by increasing the width $w_2$ of the electrode strips $2u,2d$ from $w_2$ to $w_2(1-\delta_{w2})$ and the electrode strips $4u,4d$ from $w_4$ to $w_4(1+\delta_{w4})$ with Z. Most generally $\delta_{w2}$ will not be equal to $\delta_{w4}$ though in most cases one will choose $\delta_{w2} \approx \delta_{w4}$ as in FIG. 6.

A Z-dependent change in the (w/G)-ratio thus can be achieved either by varying the plate separation G(Z) or by using tapered electrode strips of widths w(Z). However, these two variation possibilities can also be combined.

Figure 6:
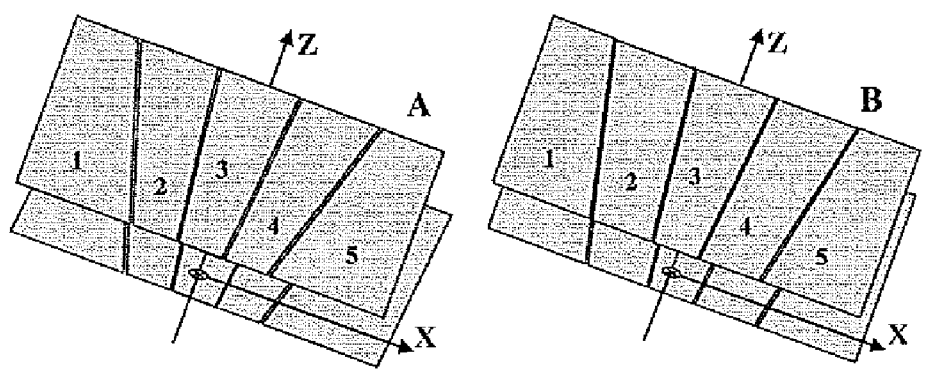
FIG. 6 illustrates an exemplary embodiment of the present invention, showing in the arrangements of electrode strips of FIG. 2 and of FIG. 5, two possible ways to use "tapered first electrode strips", i.e. examples in which with varying Z positions the widths w(Z) of the tapered first electrode strips 2,3,4 vary, which will cause multipole fields that change with Z as well as fields in Z-direction as is shown in example B. In the example A the ratio between the width w(Z) of a specific electrode strip and the separation 2G(Z) of the two plates vary such that w(Z)/G(Z), also called the w/G-ratio, is substantially independent of Z.

Two arrangements of tapered straight electrode strips are illustrated in FIG. 6 though not shown tapered curved electrode strips are possible as well. In both cases the transversal multipole strength will increase with Z. Furthermore in case B also the potential will vary along the Z-axis while in case A the potential along the Z-axis will be substantially independent of Z because the taper-angles of the different electrode strips of width w(Z) as well as the plate separation G(Z) are chosen such that the (w/G)-ratio is substantially constant.

Figure 7:
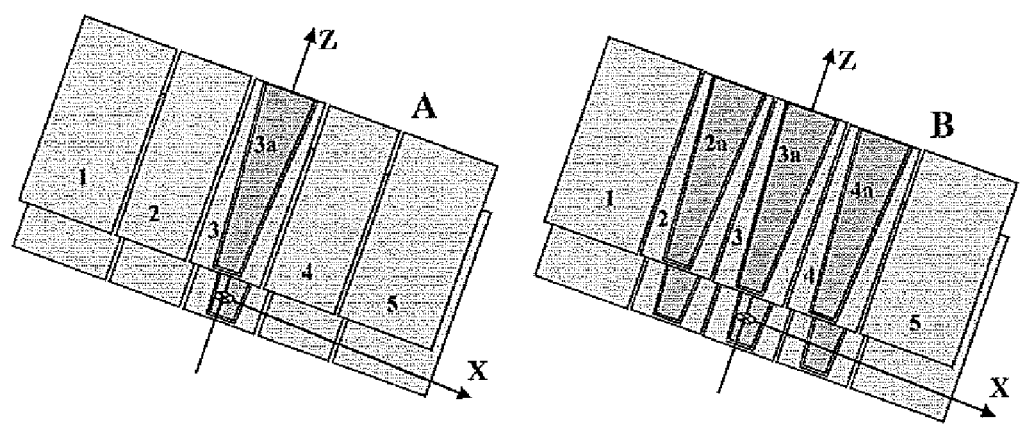

A change of the potential along the Z-axis will establish an electric DC-field in the Z-direction within the volume of a plate-multipole. Such a field is very useful when passing an ion beam along the Z-axis of an arrangement of electrode strips similar to that of FIG. 2 or FIG. 3 filled with a buffer gas. In such a case, namely the ions will lose energy by ion-atom or ion-molecule collisions and eventually stop their forward motion unless there is a gas pressure gradient or an electric field in Z-direction that will push the ions along the Z-axis. Such fields can be established by rod or ring structures in the related art, but according to the exemplary embodiment of the present invention, such a field is established by inclined or tapered electrode strips illustrated in FIG. 5, FIG. 6, and FIG. 7. Such a field can be formed by applying DC-potentials to the electrode strips 3 in the tapered electrode strip arrangement illustrated in example B of FIG. 6. Such a field in Z-direction can also be formed by the tapered electrode strip arrangement illustrated in example A of FIG. 7 if one applies to the electrode strips "3a" the RF- and DC-potentials of the electrode strip "3", plus an additional ion attracting or repelling DC-potential and in the example B of FIG. 7 if one applies to the electrode strips "2a,3a,4a" the RF- and DC-potentials of the electrode strips "2,3,4" plus additional ion attracting or repelling DC-potentials.

Figure 8:
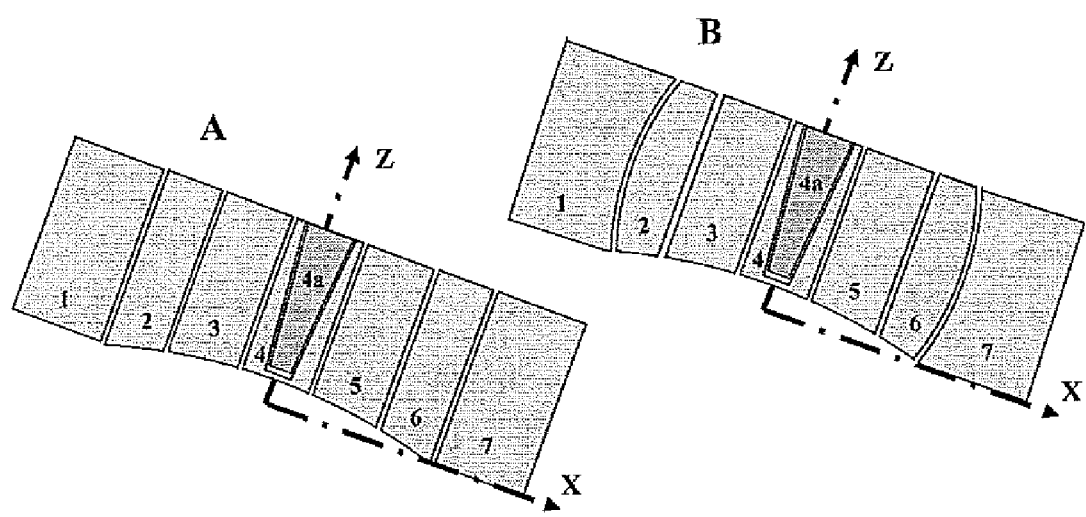
FIG. 8 illustrates an exemplary embodiment of two systems similar to FIG. 7 in which case the flat and thin first electrode strips have different average lengths which results in a curved and principally also inclined entrance or exit boundary of the plate-multipole. In example A the different electrode strips are all shown to have constant widths and thus straight sides while in example B four of the electrode strips change their widths and are shown to have straight as well as curved sides.

In some cases it is useful to change the lengths of the different electrode trips as is shown in FIG. 8 for the case of curved entrance boundaries of plate-multipoles. Such boundaries can be formed at the entrance as well as at the exit of a plate-multipole and they can be curved as is shown in FIG. 8 but they can also be inclined or noncircularly curved. All of these variations allow an additional way to control transversal forces on an ion beam.

Figure 9:
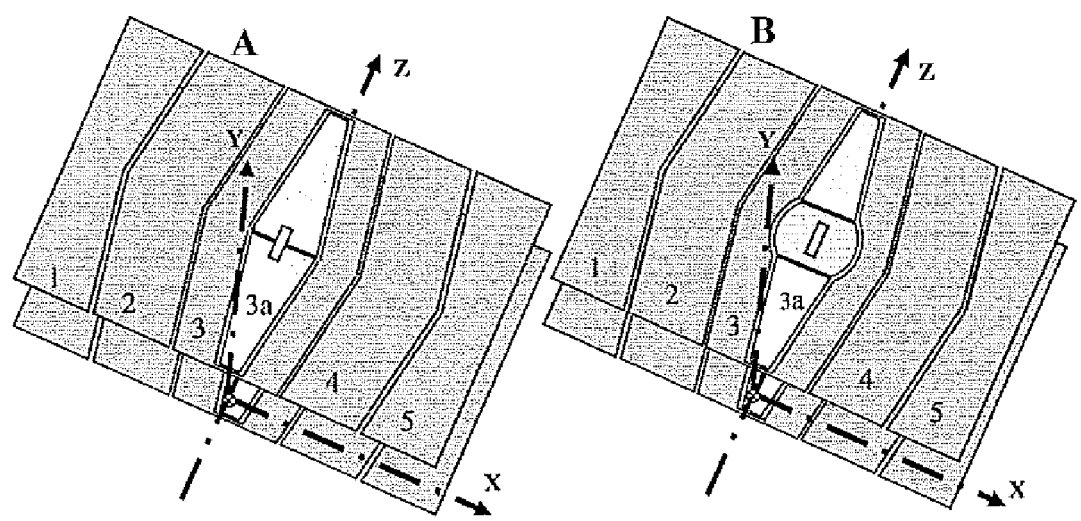
FIG. 9 illustrates an exemplary embodiment of a plate-multipole that acts similarly as the ones illustrated in FIG. 7 in which ions experience forces in Z-direction that concentrate the ions in about the middle of the shown arrangement of electrode strips if an ion attractive potential is applied additionally to these center electrode strips. In example A this is achieved by a doubly trapezoidal center electrode strip while in example B this doubly trapezoidal center electrode strip features an additional circular-like bulge which causes even stronger forces to the center of the system. Shown are also in both examples apertures through which ions can be extracted substantially perpendicularly to the first electrode strips on the upper or on the lower plate. The center electrode strips are also indicated as divided in Z-direction so that in case A, a DC field can be formed in Z-direction for a short period after the ions have been concentrated. This can also be done in case B. At a time before this ion extraction, the ions can be moved towards the middle of the bulged area.

A special variation of the principle of tapered electrode strips is shown in FIG. 9. In this case electrode strips are shown that are doubly tapered so that DC-potentials added to these electrode strips will cause forces that are directed towards a middle Z-position. This method can be applied to straight-axis-section plate-multipoles as well as to curved-axis-section plate-multipoles. In both cases ions will be brought together as a small cloud at a middle Z-position. From this position then the ions can be extracted either in 1. the Y-direction through the in FIG. 9 shown extraction orifice which may be rectangular as shown in FIG. 9 or shaped differently to allow optimal ion extraction which is achieved by applying for a short time different potentials to the electrode strips on the upper and the electrode strips on the lower plate.
2. in X-direction by applying for a short period different potentials to the different electrode strips characterized by different X-positions where, however, the potentials that for a short period are applied to electrode strips on the upper plate and the potentials that are applied for a short period applied to electrode strips on the lower plate are substantially identical. This ion extraction in X-direction may be especially useful in case of a curved-axis section where it would tend to concentrate the ion cloud if the extraction would occur in the concave direction and dispersed the ions if the extraction would occur in the convex direction.
3. in Z-direction by applying a field in Z-direction which can be formed by different potentials applied to fringe-field limiters at the entrance and exit of the plate-multipole or by dividing the doubly tapered electrode strip in two tapered one the first of which increases its width with Z while the second one reduces its widths with Z. In such a case one then can for a short period apply different DC-potentials to the two tapered electrode strips.

Figure 10:
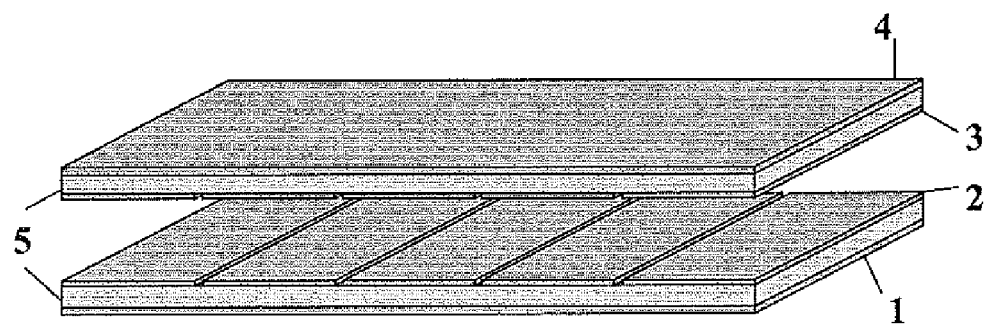
FIG. 10 illustrates an exemplary embodiment in which the flat and thin first electrode strips (2,3) are built as metal patches on some insulating or slightly conductive substrate (5) formed in the technique of etched printed circuit boards. In the shown example also grounded shielding (1,4) of the active arrangement of electrode strips is provided.

A multipole with or without a superimposed dipole field can be built according to FIGS. 2-9 with the electrode strips on the "plates" being formed in different ways. They can:

1. be built from insulated metal pieces, where these electrode strips should be mounted such that the mounting structure can not or only slightly be viewed from the position of the ions
2. be built from insulated metal wires to which potentials are applied that are either different for each wire or different for different groups of wires. This design can be advantageous if the space in which the ions move must be well pumped so that the final vacuum is very low.
3. be built as metal patches on printed circuit boards (see FIG. 10) placed for instance on ceramic-substrate material or on an epoxy-substrate material which for most application should be selected such as to have a low outgas factor. This is an elegant way that features high precision alignment of the electrode strips. This arrangement also allows an effective shielding of the RF-fields by placing grounded conductive layers on the opposite side of the substrate material as is shown in FIG. 10. Using multiple layered printed circuit boards this shielding layer can be placed in the middle of the thickness of the substrate. In this technique also a double or multiple layered shielding is possible. In case of a printed circuit board construction it is advantageous if the different electrode strips are separated by only small gaps—gaps that best are smaller than the thickness of the metal patches—so that a charging of insulating substrate material has only a small effect on the overall potential distribution.

4. be built as metal patches on printed circuit boards that are slightly conductive. This can be achieved by depositing some slightly conductive film over the whole printed circuit board, or by using a slightly conductive base material like the so called "green ceramic". In this case, the potential between different electrode patches is linearly interpolated.

A property of a plate-multipole is that the potential $V_{N0}$ of any multipole potential distribution as described by Eq. (1) can easily be varied, and thus the strength of the corresponding multipole. This can be done either permanently for a DC-component or as a function of time. Thus it is especially possible to alter the strengths of the multipole fields with the same or another frequency or phase-shift as the dipole field. This allows for instance to add to a multipole field of one frequency a rotating field of another frequency. This arrangement can be useful for the fragmentation of molecule ions [V. Raznikov et al., Rap. Comm. in Mass Spectrom. 15 (2001) 1912].

Also, one can change any of these frequencies with time. This can be advantageous, for example, for a mobility spectrometer or a differential mobility spectrometer, so that ions of lower and of higher masses can experience different focusing strengths. Moreover, plate-multipoles in which the dominant polarity is that of a quadrupole are flexible devices that can produce quadrupoles of variable strength or tilt-angle $\Phi$ with values being chosen to be permanent or to be changed with time.

Furthermore one can drive a plate-multipole not by frequencies but rather by quickly switched voltages as has been done for instance in a digital ion trap [P. H. Dawson, "Quadrupole Mass Spectrometry and its Application", Elsevier, Amsterdam 1976] constructed of rod-type electrodes. This can be especially useful if complex mixtures of frequencies would be required otherwise and if constant or pulsed DC-potentials must be added to the system as well.

Figure 11:
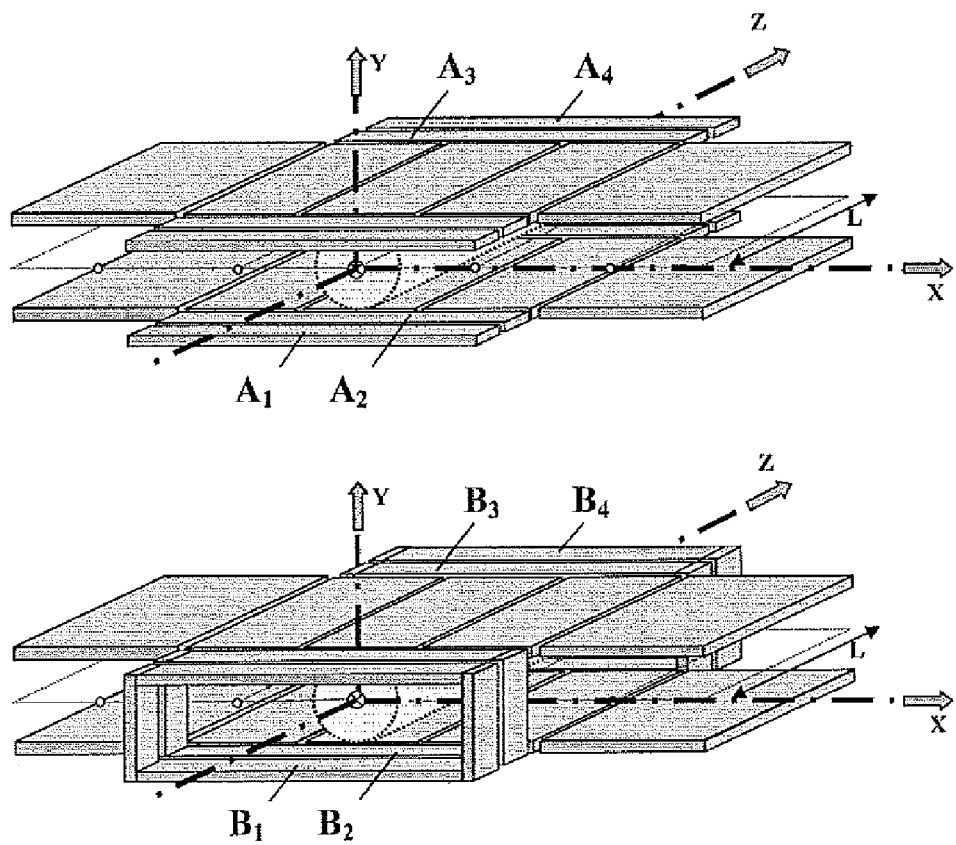
FIG. 11 illustrates fringe-field limiters placed after as well as before a plate-multipole. In example A two such fringe-field limiters are shown on each end of the plate-multipole with all limiters $A_1, A_2, A_3, A_4$ formed in a slit-type construction. In example B two such fringe-field limiters are shown on each end of the plate-multipole with all $B_1, B_2, B_3, B_4$ formed in a frame construction.
Figure 12:
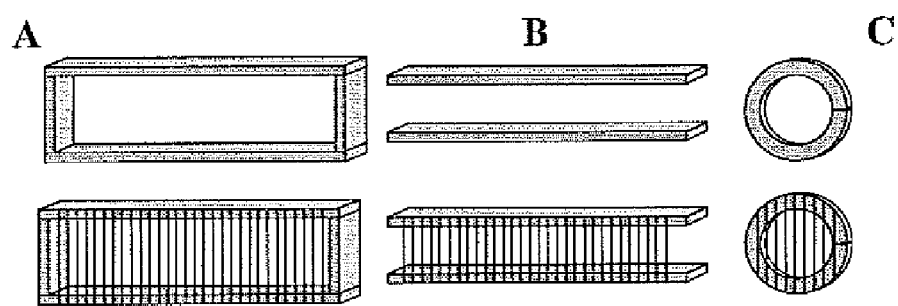
FIG. 12 illustrates fringe-field limiters of (A) the rectangular frame-type, (B) the slit-type, and (C) the circular ring type. All examples are shown with and without wire grids which also could be replaced by meshed grids.

Plate-multipoles are often terminated by fringe-field limiters as is shown for two shapes of them in FIG. 11. Such fringe-field limiters avoid that the fields created in a plate-multipole extent too far out of the plate-multipole. Such fringe-field limiters are shown in FIG. 12. They can a. be built as a rectangular, circular or elliptical frames
b. be built as a "slit-type" diaphragm which can easily be integrated in the design of a multipole that is formed as a printed circuit board All these diaphragms can also be limited by grids, as is shown in FIG. 12, in which case the structure of the frame has only a minor importance.

If one applies substantially the same potential to the electrode strips $A_2,A_3$ or $B_2,B_3$ as the potential at the XZ-reference-plane, the field of the plate-multipole would be reasonably terminated. The electrode strips $A_1,A_4$ or $B_1,B_4$ could be omitted in this case. There are, however, other uses of these fringe-field limiters 1. Applying an ion repelling DC-potential to the electrodes $A_2,A_3$ or $B_2,B_3$ the ions, that are already in the volume of the plate-multipole, can not escape and will move back and forth along the Z-axis. Thus if the proper potentials are applied to the electrode-strips the plate-multipole could be used as an ion trap which can simply keep ions, mass analyze them or prepare them for a bunched extraction in X-, Y, or Z-direction as described already above when discussing FIG. 9. Such a trapping action could also be assisted or as stated already achieved alone by doubly tapered electrode-strips.

2. Applying an ion attracting DC-potential to the electrodes $A_3$ or $B_3$ at the exit sides of the plate-multipoles shown in FIG. 11 and an ion repelling DC-potential to the electrodes $A_4$ or $B_4$ one would find that the a short ion trapping region would be formed from which the ions can be extracted in Z-direction by simply changing the potential of the electrode strips $A_4$ or $B_4$ to an ion attracting potential. Plate-multipoles can be used for different applications which will be outlined below and which are illustrated in part in FIG. 13 and in FIG. 14. though there are many other combinations in which they can be used.

1. A plate-multipoles can transportions from one section to the next. This may only be a physical separation along the Z-axis or may move the ions from one type of analysis to another.

2. A plate-multipole can be used as a beam cooler in which ions lose energy by ion-atom or ion-molecule collisions so that the ion cloud is compressed to a smaller phase-space volume. This can be done by simply passing the ions once through the length of a plate-multipole or by trapping the ions as discussed above when discussing FIG. 11.

3. A plate-multipole can be used as a collision cell in which molecule ions are fragmented by ion-atom or ion-molecule collisions. The resultant ion fragments then can be mass-analyzed in some sector field analyzer, a quadrupole filter, or a time-of-flight mass spectrometer. This fragmentation of molecule ions can be achieved by simply passing the ions once through the length of the plate-multipole used as an ion collision cell or by trapping the ions as discussed above when discussing FIG. 11.

4. A plate-multipole can be used as a quadrupole mass analyzer. This mass analysis can be achieved by simply passing the ions once through the length of the plate-multipole in which case one would speak of a mass filter. However, one can also achieve the mass analysis by using the plate-multipole as a mass analyzing ion trap in which case one would trap the ions as discussed above when discussing FIG. 11.

In cases 1, 2, 3 it is sufficient for most cases to apply to the different electrodes strips only RF-voltages. In this case, however, only low mass ions would be eliminated while all other ions can pass. Applying additionally also DC-voltages to the different electrode strips only ions of a specific usually short mass range will survive. In the cases 2 and 3 such mass analyzing capabilities can also be implemented by applying not only RF- but also DC-potentials to the different electrode strips. In these cases, however, usually limited mass analyzing capabilities suffice.

Figure 13:
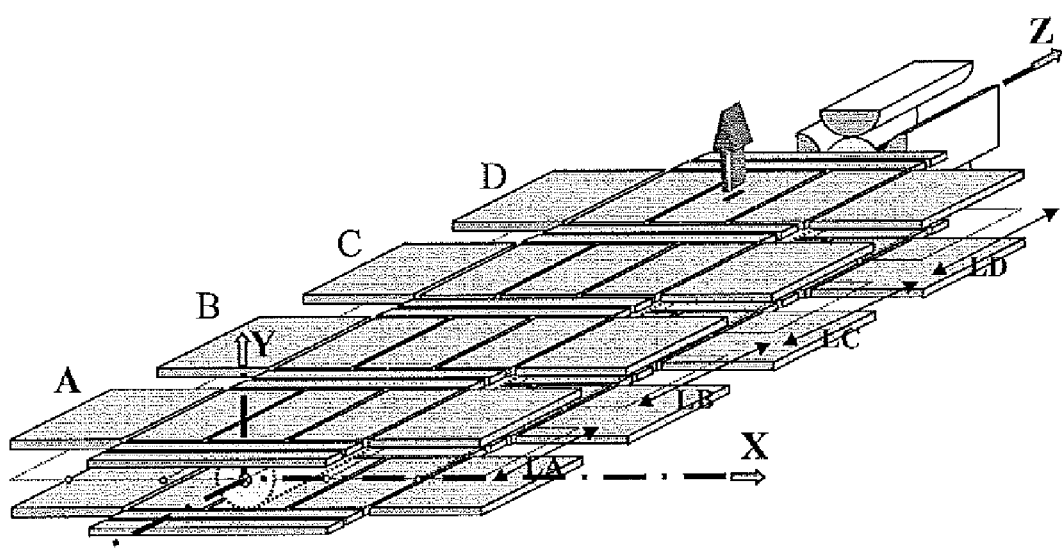
FIG. 13 illustrates the combination of four plate-multipoles A,B,C,D and a related art rod-type quadrupole mass analyzer all arranged along the same straight Z-axis. In the shown example the rod-type quadrupole is arranged downstream of plate-multipole D though it could be arranged between any two of the plate-multipoles. The plate-multipoles are all shown to be separated by slit-type fringe-field limiters, though these limiters could be reduced to one between two plate-multipoles, left off completely or changed to other types of fringe-field limiters. Shown is also that ions could be extracted perpendicularly to the plate-multipole D.
Figure 14:
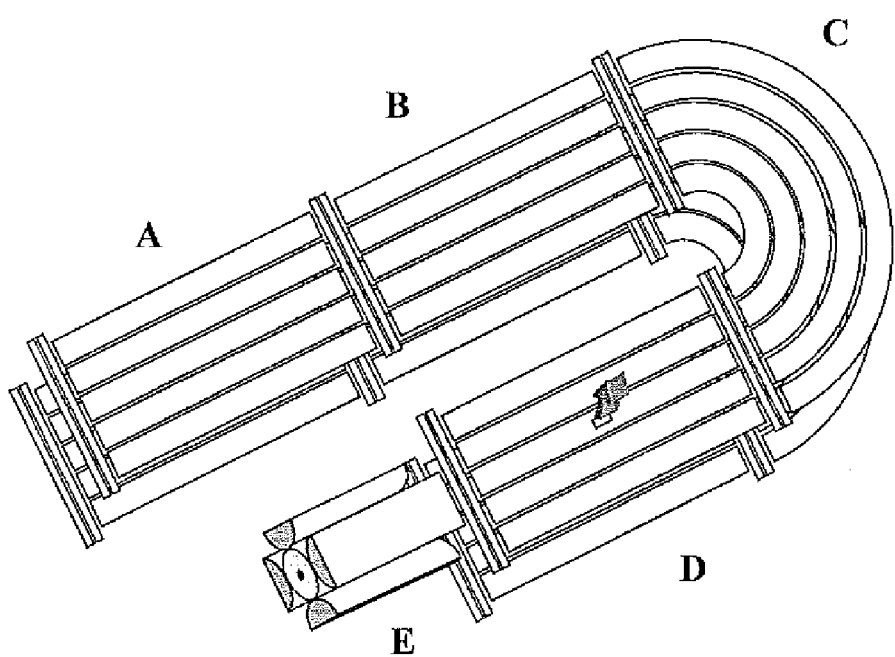
FIG. 14 illustrates the combination of several plate-multipoles all of which are characterized by straight Z-axes except the multipole C which discloses a curved Z-axis. This plate-multipole would be especially suited to be used as a collision cell in which molecular ions are fragmented by ion-atom or ion-molecule collisions which for example could be mass analyzed in the plate-multipole D, if the proper RF- and DC-potentials would be applied to the electrode strips, so that the system would operate as a RF-quadrupole filter or a mass analyzing linear ion trap. The plate-multipole D, however, could also be used as a plate-multipole that concentrates the ions to its middle and ejects them perpendicular to its upper plate or transfers the ion beam to a rod-type quadrupole mass analyzer.

Combinations of different plate-multipoles are shown in FIG. 13 and in FIG. 14. In both figures the tasks the different plate-multipoles must perform are not fix. Some feasible arrangements are proposed in the descriptions below. Many other possibilities exist, however.

In FIG. 13 there are 4 plate-multipoles A,B,C,D to which a related art rod-type quadrupole is added on the same Z-axis. In this arrangement one could possibly use the plate-multipole A as a mobility spectrometer, the plate-multipole B as a transfer section, the plate-multipole C as mass analyzer, the plate-multipole D as a collision cell to fragment molecule ions which then move into a final rod-type quadrupole mass analyzer. However, it also is indicated that ions could have been extracted from plate-multipole D perpendicular to the plates for instance to be injected into a not shown time-of-flight mass analyzer.

Additional plate-multipoles could be placed into the arrangement shown in FIG. 13 for instance as transfer devices that would for instance separate the different analyzers better or that would provide additional capabilities like beam cooling. Naturally the rod-type quadrupole mass analyzer could also be placed between two plate-multipoles instead of being added after plate-multipole D. All plate-multipoles are shown as being separated by fringe-field limiters which could by simplified if needed or which could be used as ion repellers so that the corresponding plate-multipole would be used as an ion trap.

In FIG. 14 a similar arrangement of plate-multipoles is shown as in FIG. 13. In this case, however, one of the plate-multipoles is shown to be a curved-axis plate-multipole is shown explicitly. For convenience, the angle of deflection of this curved-axis plate-multipole has been chosen to be 7c, though any other angle could have been chosen as well. If this curved-axis multipole C is used as a collision cell, the plate-multipole D could be used as a mass analyzer or as a transfer device to another mass analyzer (not shown), if the proper RF- and DC-potentials are applied to its electrode strips. The plate-multipole D could also be used as a plate-multipole that concentrates the ions to its middle and ejects them perpendicular to its upper plate, for instance into a time-of-flight mass analyzer. However, this plate-multipole D could also be used as a transfer device to another mass analyzer, like the one shown as a related art rod-type quadrupole. In such a case, one could, for instance, operate the plate-multipole A as a beam cooler and the plate-multipole B as a mass analyzer that selects precursor ions of a specific molecule mass to be fragmented in a collision cell, which here would be the plate-multipole C.

Figure 15:
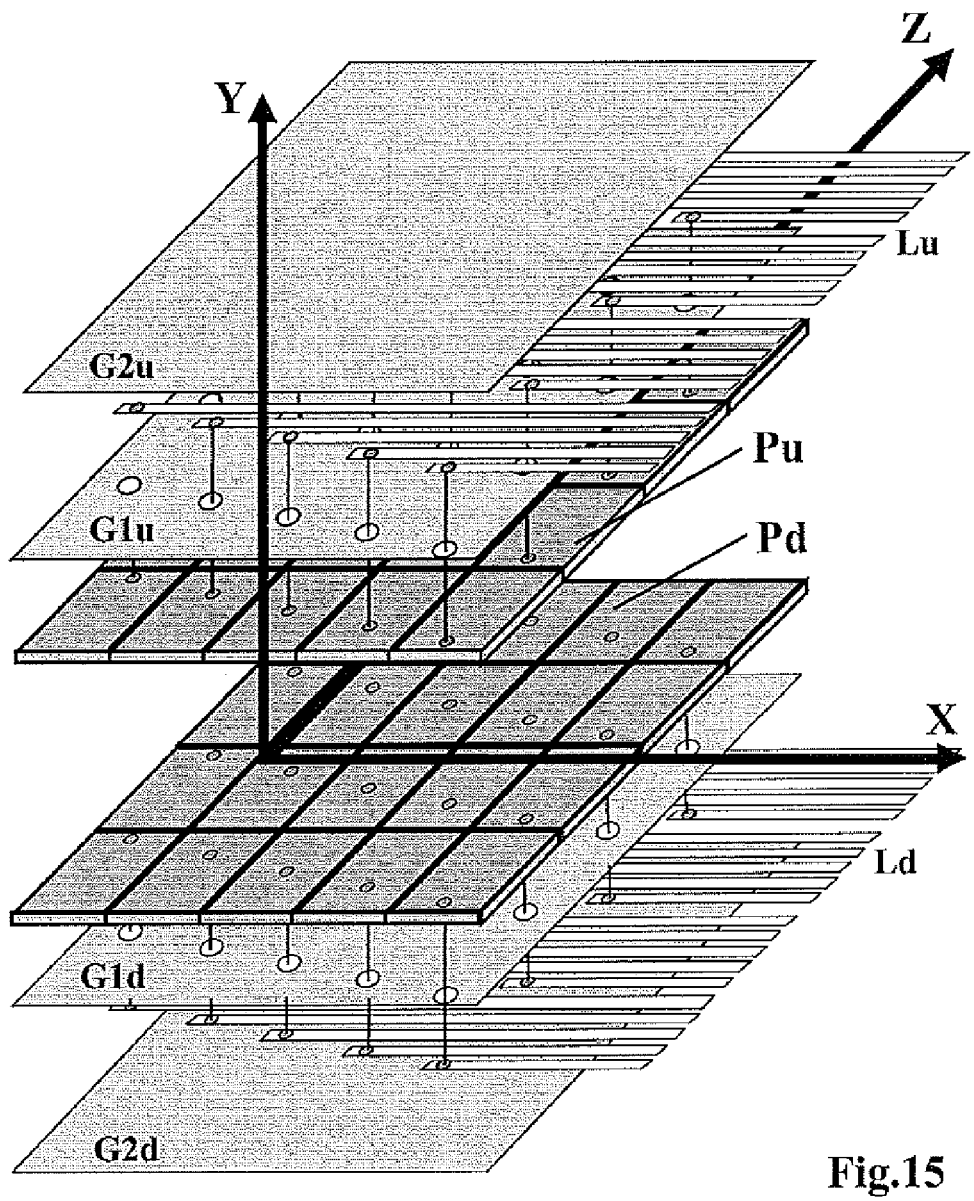
FIG. 15 illustrates 5 electrode strips on two parallel plates Pu and Pd, which are segmented in Z-direction. This configuration allows application of X-dependent DC- and RF-potentials to all electrode strips that are characterized by a certain X-value, and to add Z-dependent RF- and DC-potentials to the potentials of all electrode strips that are characterized by a specific Z-value.

FIG. 15 shows 5 electrode strips on two parallel plates Pu and Pd located at 5 different X-values and all arranged parallel to the Z-axis (see also FIG. 2). In FIG. 15, however, these 5 electrode strips are divided in 4 sections characterized by different average Z-values. In this exemplary embodiment, it is intended to apply corresponding X-dependent DC- and RF-potentials to all electrode strips that are characterized by a certain X-value and to add substantially the same Z-dependent RF- and DC-potential to these potentials for all electrode strips that are characterized by a certain Z-value. Since this addition should be done for the electrode strips at Pu and Pd, one can establish a DC-field in Z-direction.

Since there are substantially many wires that supply all the different potentials to the different electrode strips, it is herein shown how this task can be performed by using leads Lu and Ld located between grounded plates G2u, G1u and G1d, G2d, respectively. This would allow the leads to be formed in the strip-line technique, and at the same time provide efficient RF-shielding of the formed RF-fields by the different electrode strips. This structure can be built in the technique of multilayered printed circuit boards. In this case, insulating triple substrates are necessary for the upper plate Pu as well as for the lower plate Pd. These substrates are not shown, however, for the sake of simplicity and clarity in the present illustration.

Figure 16:
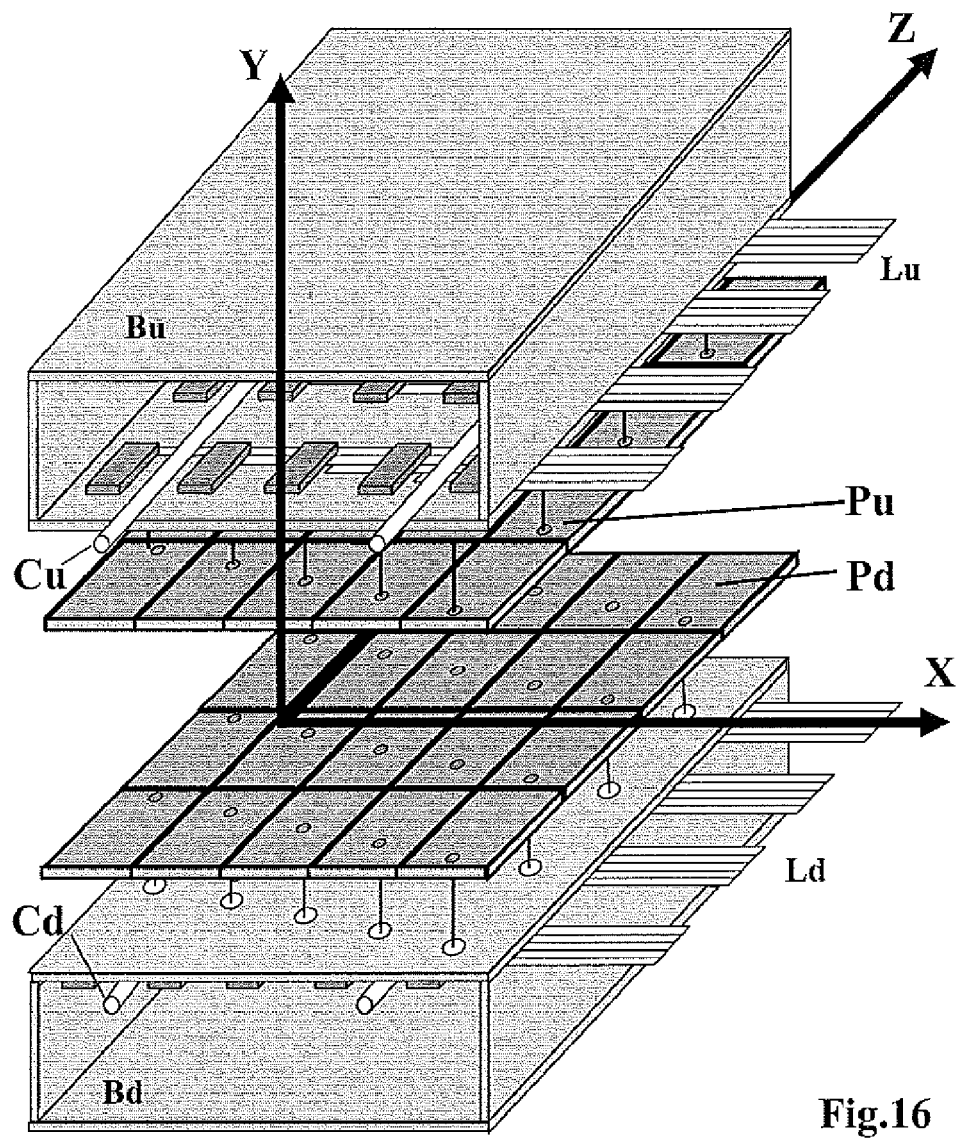
FIG. 16 illustrates 5 in-Z-direction segmented and placed on two parallel plates Pu and Pd as shown in FIG. 15.

In FIG. 16 also, 5 in-Z-direction segmented electrode strips are shown on two parallel plates Pu and Pd as shown in FIG. 15. In the shown case, the final active voltage control elements are placed substantially close to the corresponding final electrode strips, so that the leads do not form additional capacitances to ground, as well as no additional resistive loads. Such an arrangement can reduce the magnitude of the required RF-power as well as the RF-fields in the rest of the ion optical system. Such an embodiment, however, may require provision of cooling by water or some other liquid to the printed circuit board on which these active elements are placed. Such cooling tubes are shown as Cu and Cd. These active elements are shown to be housed in an enclosure in which the residual gas pressure can differ from that in the region in which the ions move.

Figure 17:
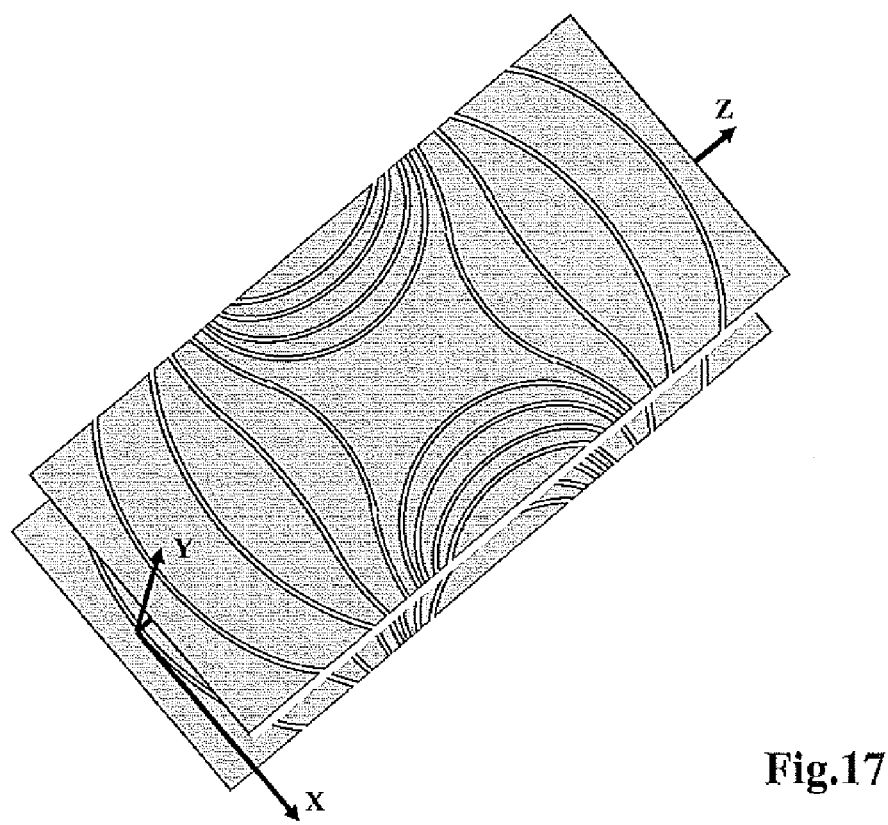
FIG. 17 illustrates electrode strips formed such that they can produce the field of an Einzel-lens if the appropriate RF- or DC-potentials are applied to the corresponding electrodes. In the same fashion, an "immersion lens" could be produced, as well as the field of an ion mirror, which are both commonly formed only by rotationally symmetric electrodes.

FIG. 17 shows electrode strips that are formed such that they can produce the field of a rotationally symmetric accelerating or decelerating lens if the correct RF- or DC-potentials are applied to the corresponding electrodes. In this case the ions will start from a potential $V_0$ then be accelerated or decelerated to a potential $V_m$ after which they are decelerated or accelerated to a potential $V_1$. In case of $V_1 \pm V_0$ one would speak of a rotationally symmetric immersion lens, and in case of $V_1 = V_0$, one would speak of a rotationally symmetric Einzel-lens.

In a similar arrangement of electrode strips also the field of a rotationally symmetric ion mirror could be produced as is known in related art ion mirrors for time of flight mass spectrometers in which case, however, this field is commonly produced by rotationally symmetric electrodes.

The foregoing embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

The invention claimed is:

1. A system for guiding an ion beam along a substantially continuous beam axis through at least one field that exerts a force on ions in said ion beam, said system comprising:
    at least one section comprising a substantially flat plate-multipole having an upper flat plate and a lower flat plate, wherein said force is one of substantially symmetric in a parallel direction and substantially antisymmetric in a perpendicular direction with respect to a plane that includes the beam axis,
    each of said upper flat plate and said lower flat plate comprising a plurality of first electrode strips having corresponding potentials, said first electrode strips generating at least a portion of said at least one field,
    wherein a fringe-field boundary is located at each end of said at least one section, and said first electrode strips are substantially thin and flat.

2. The system of claim 1, wherein said upper flat plate and said lower flat plate are positioned one of substantially parallel and inclined to said plane in said at least one section where an extrapolated intersection line of said upper flat plate and said lower flat plate is substantially perpendicular to the ion beam axis.

3. The system of claim 1, wherein said at least one section comprises at least one of a straight section and a curved section that is curved within said plane, and wherein the straight ones of said at least one section include substantially quadrilateral ones of said first electrode strips parallel to the ion-beam axis, and curved ones of said at least one section include substantially curved ones of said first electrode strips having a substantially constant distance from the ion-beam axis.

4. The system of claim 1, wherein said ion-beam axis at said at least one section is at least one of straight, curved, and curvilinear.

5. The system of claim 1, wherein each of the first electrode strips have at least one of (a) a straight edge and (b) a curved edge, and wherein the width substantially perpendicular to the ion-beam axis is less than the length along the ion-beam axis for each of the first electrode strips.

6. The system of claim 5, where one of the lengths and the angles of deflection of the first electrode strips are equal with respect to at least one adjacent one of the first electrode strips.

7. The system of claim 5, where one of the lengths and the angles of deflection of the first electrode strips are not equal with respect to at least one adjacent one of the first electrode strips, and vary one of linearly and non-linearly with their respective distances from the ion-beam axis.

8. The system of claim 1, wherein the width of at least one of said first electrode strips increases along the ion-beam axis.

9. The system of claim 8, wherein a ratio of the widths of the first electrode strips with respect to a distance between the upper flat plate and the lower flat plate is one of constant and variable along the ion-beam axis.

10. The system of claim 8, wherein potentials are applied to at least two of the first electrode strips for a period, so as to form a field along the ion-beam axis.

11. The system of claim 1, wherein the width of at least one of said first electrode strips increases and decreases along the ion-beam axis, such that the width is maximized at a middle portion.

12. The system of claim 1, wherein widths of ones of said first electrode strips are greater at further distances from said ion beam.

13. The system of claim 1, wherein the width of a central one of said first electrode strips is equal or greater than the widths of adjacent ones of the first electrode strips.

14. The system of claim 1, wherein said ions are directed toward one of said upper flat plate and said lower flat plate having a greater ion-attracting potential applied thereto for a period, and an aperture therein so as to permit emission of at least a portion of said ions.

15. The system of claim 1, wherein said ions are directed along said plane by different potentials applied to said first electrode strips to form a field parallel to said plane, for a period.

16. The system of claim 1, further comprising a plurality of second electrode strips positioned substantially perpendicular to said plane at a first surface and a second surface, wherein said second electrode strips are substantially thin and flat.

17. The system of claim 16, wherein said second electrode strips are one of (a) substantially quadrilateral and (b) substantially curved and having a constant minimal distance from said ion-beam axis.

18. The system of claim 16, wherein widths of said second electrode strips are greater at distances further from said plane.

19. The system of claim 16, wherein the width of at least one of said second electrode strips increases along the ion-beam axis.

20. The system of claim 16, wherein the width of at least one of said second electrode strips increases and decreases along the ion-beam axis, such that the width is maximized at a middle portion.

21. The system of claim 16, wherein said ions are directed toward one of said first surface and said second surface having a greater ion-attracting potential applied to said second electrode strips thereat for a period, and an aperture in said first surface and said second surface to permit emission of at least a portion of said ions.

22. The system of claim 16, wherein the plate-multipole is used for ion beam transport in a low-pressure buffer-gas, in a vacuum ion-transport system in which the residual gas pressure is so low that an ion experiences substantially minimal ion-atom or ion-molecule collisions, wherein RF multipole fields and DC multipole fields are formed as to provide mass analyzing capabilities, and a distance between said first surface and said second surface is substantially less than a distance between said upper flat plate and said lower flat plate.

23. The system of claim 16, wherein at least one of (a) substantially constant potentials and (b) sinusoidal potentials are applied to each of said second electrode strips.

24. The system of claim 16, wherein at least one of (a) substantially constant potentials and (b) rectangularly switched potentials are applied to each of said second electrode strips.

25. The system of claim 16, wherein at least one of said RF potentials comprises at least one frequency applied to one of said second electrode strips, and each said at least one frequency can vary with respect to each other in at least one of amplitude and phase.

26. The system of claim 1, wherein said first electrode strips comprise one of conductive material and material that has a conductive surface, such that the potential along each of said electrode strips is substantially constant.

27. The system of claim 1, wherein the first electrode strips are formed as groups of one or more wires.

28. The system of claim 1, wherein the first electrode strips comprise patches of conductive material on respective insulating or slightly conducting substrates, and are formed as printed circuit boards.

29. The system of claim 28, wherein said patches are separated by an area that is less than or equal to a thickness of any one of said first electrode strips.

30. The system of claim 28, further comprising at least one conductive layer that is configured to shield a high-frequency field formed by said patches if RF potentials are applied.

31. The system of claim 1, wherein at least one of said RF potentials comprises at least one frequency applied to one of said first electrode strips, and each said at least one frequency can vary with respect to each other in at least one of amplitude and phase.

32. The system of claim 31, wherein at least the dipole field is modulated by a frequency independent of other multipole fields for said at least one section.

33. The system of claim 1, wherein at least one of (a) substantially constant potentials and (b) sinusoidal potentials are applied to each of said first electrode strips.

34. The system of claim 1, wherein at least one of (a) substantially constant potentials and (b) rectangularly switched potentials are applied to each of said first electrode strips.

35. The system of claim 1, wherein outer ones of said first electrode strips are at a common potential, and non-central inner ones of said first electrode strip's have a substantially greater potential than said common potential, and a central one of said first electrode strips has a substantially lesser potential than that of said inner ones of said first electrode strips.

36. The system of claim 1, wherein the plate-multipole is used for ion beam focusing toward said plane in a high-pressure buffer-gas from several bar to below 1 mbar in an ion mobility spectrometer (IMS) or in a differential mobility spectrometer (DMS), wherein RF multipole fields and DC multipole fields are provided by said plate-multipole as said ions travel along said ion-beam axis.

37. The system of claim 1, wherein the plate-multipole is used for ion beam transport in a medium-pressure buffer-gas from about 1 mbar to below 1 μbar in a beam cooler in which the ions lose energy in ion-atom or ion-molecule collisions so that the phase-space of the ion beam is reduced wherein RF multipole fields are provided at said plate-multipole as said ions travel along said ion beam axis.

38. The system of claim 1, wherein the plate-multipole is used for ion beam transport in a medium-pressure buffer-gas from about 1 mbar to below 1 μbar in a collision chamber in which molecules are fragmented in ion-atom or ion-molecule collisions and fragment ions are extracted.

39. The system of claim 1, wherein the plate-multipole is used for ion beam transport in a low-pressure buffer-gas, in a vacuum ion-transport system in which the residual gas pressure is so low that an ion experiences substantially minimal ion-atom or ion-molecule collisions, and wherein RF multipole fields and DC multipole fields are formed as to provide mass analyzing capabilities.

40. The system of claim 1, wherein the field of the plate-multipoles is limited by substantially rectangular, rotational, slit-type electrodes or grids placed at potentials that are ion repelling relative to the ion-beam axis, so that ions inside the plate-multipole are trapped as in a linear quadrupole ion trap, and wherein RF multipole fields and DC multipole fields are formed as to provide mass analyzing capabilities.

41. The system of claim 1, wherein the length of at least one of the first electrode strips is divided into at least two sections to which different RF- and DC-potentials are added such that a field along the ion beam is established.

42. The system of claim 16, wherein the length of at least one of the second electrode strips is divided into at least two sections to which different RF- and DC-potentials are added such that a field along the ion beam is established.

43. The system of claim 1, wherein at least one of the first electrode strips is bent within the plates with said at least one of the first electrode strips being located such that it approximates the shape of one of an equipotential line of an Einzel-lens, an accelerating-lens, and an ion mirror.

44. The system of claim 16, wherein at least one of the second electrode strips is bent within the ortho-surfaces with said at least one of the second electrode strips being located such that it approximates the shape of one of an equipotential line of an Einzel-lens, an accelerating-lens, and an ion mirror.

45. The system of claim 1, wherein the potentials supplied to different ones of said first electrode strips of at least one plate-multipole are supplied by leads placed between at least two grounded layers in a multilayer printed circuit board.

46. The system of claim 1, wherein the potentials to different ones of said electrode strips of at least one plate-multipole are supplied by active electronic elements placed on that printed circuit board to which the electrode strips are mounted.

47. The system of claim 1, wherein the potentials to different ones of said first electrode strips of at least one plate-multipole are supplied by active electronic elements placed in a box the residual gas pressure within which can differ from that in which the ions move.

48. The system of claim 46, wherein the printed circuit boards are water cooled.

49. The system of claim 47, wherein the printed circuit boards are water cooled.

50. The system of claim 1 wherein the first electrode strips are formed to provide the potential distribution of a rotationally symmetric electrostatic lens, or of a rotationally symmetric ion mirror, provided that proper potentials are applied to the electrode strips.

\* \* \* \* \*